(12) United States Patent
Kini et al.

(10) Patent No.: US 11,566,008 B2
(45) Date of Patent: Jan. 31, 2023

(54) CRYSTALLINE FORM OF 4-AMINO-N-TERT-BUTYL-4,5-DIHYDRO-3-ISOPROPYL-5-OXO-1,2,4-1H-TRIAZOLE-1-CARBOXAMIDE AND A PROCESS FOR PRODUCING THEREOF

(71) Applicant: UPL Limited, Maharashtra (IN)

(72) Inventors: Prashant Vasant Kini, Mumbai (IN); Ajay Sadashiv Chhatre, Mumbai (IN)

(73) Assignee: UPL LIMITED, Mumbai (IN)

( * ) Notice: Subject to any disclaimer, the term of this patent is extended or adjusted under 35 U.S.C. 154(b) by 0 days.

(21) Appl. No.: 17/402,612

(22) Filed: Aug. 16, 2021

(65) Prior Publication Data
US 2022/0048871 A1    Feb. 17, 2022

(30) Foreign Application Priority Data
Aug. 14, 2020   (IN) .............................. 202021035020

(51) Int. Cl.
*C07D 249/12*    (2006.01)
*A01N 43/653*    (2006.01)

(52) U.S. Cl.
CPC .......... *C07D 249/12* (2013.01); *A01N 43/653* (2013.01); *C07B 2200/13* (2013.01)

(58) Field of Classification Search
CPC .................................................... C07D 249/12
See application file for complete search history.

(56) References Cited

FOREIGN PATENT DOCUMENTS

WO    WO-2017152712 A1 *  9/2017    ............. A01N 47/38

* cited by examiner

*Primary Examiner* — Shawquia Jackson
(74) *Attorney, Agent, or Firm* — IP Pundit LLC

(57) ABSTRACT

The invention provides a novel crystalline form of 4-amino-N-tert-butyl-4,5-dihydro-3-isopropyl-5-oxo-1,2,4-1H-triazole-1-carboxamide and a process for preparation of said crystalline form. The invention also relates to formulations and method for controlling weeds using said formulations.

12 Claims, 5 Drawing Sheets

CRYSTALLINE FORM OF 4-AMINO-N-TERT-BUTYL-4,5-DIHYDRO-3-ISOPROPYL-5-OXO-1,2,4-1H-TRIAZOLE-1-CARBOXAMIDE AND A PROCESS FOR PRODUCING THEREOF

FIELD OF THE INVENTION

The present relates to a novel crystalline form of 4-amino-N-tert-butyl-4,5-dihydro-3-isopropyl-5-oxo-1,2,4-1H-triazole-1-carboxamide and a process for preparation of said crystalline form. The disclosure also relates to formulations and method for plant protection using said formulations.

BACKGROUND 4-amino-N-tert-butyl-4,5-dihydro-3-isopropyl-5-oxo-1,2,4-1H-triazole-1-carboxamide (Amicarbazone) is a herbicidal active substance of the formula I with a broad spectrum of weed control.

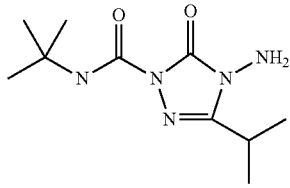

Formula I

Amicarbazone exists in different crystalline forms. Acta Crystallographica Section E: Structure Reports 2013 discloses a crystalline form of amicarbazone in which three independent molecules comprise the asymmetric unit of the molecule (Z=6). The form is referred to as amicarbazone Form A hereinafter.

WO2017152712 discloses a crystalline form of amicarbazone prepared from amorphous form of amicarbazone.

Different crystalline forms of the same active substance often display different properties. Stability, solubility, suspensibility, dispersibility, crystal density, crystal hardness and dissolution rate are some of the properties that vary with difference in crystalline nature of the active substance.

Stability of a crystalline form is significant in terms of stability on storage, suspension stability, stability to decomposition as well as with respect to conversion of one form to another. Biological activity of different forms of an active substance depends on many of the parameters described above. The stability, dispersibility and solubility of formulations prepared from known crystalline forms of amicarbazone was not satisfactory.

It is surprisingly found by the present inventors that by defined processes, a previously unknown, stable crystalline form of 4-amino-N-tert-butyl-4,5-dihydro-3-isopropyl-5-oxo-1,2,4-1H-triazole-1-carboxamide is obtained that is advantageous for preparing improved formulation products useful in agriculture.

OBJECTS OF INVENTION

It is an object to provide a novel crystalline form of 4-amino-N-tert-butyl-4,5-dihydro-3-isopropyl-5-oxo-1,2,4-1H-triazole-1-carboxamide.

Another object is to provide a process for preparing a crystalline form of 4-amino-N-tert-butyl-4,5-dihydro-3-isopropyl-5-oxo-1,2,4-1H-triazole-1-carboxamide.

It is another object to provide an agriculture formulation comprising a crystalline form of 4-amino-N-tert-butyl-4,5-dihydro-3-isopropyl-5-oxo-1,2,4-1H-triazole-1-carboxamide.

SUMMARY OF INVENTION

In an aspect the present disclosure provides a novel crystalline form of 4-amino-N-tert-butyl-4,5-dihydro-3-isopropyl-5-oxo-1,2,4-1H-triazole-1-carboxamide.

In another aspect the present disclosure provides a crystalline form of 4-amino-N-tert-butyl-4,5-dihydro-3-isopropyl-5-oxo-1,2,4-1H-triazole carboxamide, characterized by an X-ray powder diffractogram using Cu-Kα radiation displays at least three of the following reflections, quoted as degrees 2θ (±0.2 degrees) values 6.8, 7.0, 7.6, 8.3, 11.2, 11.3, 12.4, 12.8, 15.6, 16.5, 16.6, 17.4, 17.5, 18.5, 19.6, 20.1, 23.5, 24.2 and 26.7.

In another aspect the present disclosure provides a crystalline form C of 4-amino-N-tert-butyl-4,5-dihydro-3-isopropyl-5-oxo-1,2,4-1H-triazole-1-carboxamide, which in an X-ray powder diffractogram using Cu-Kα radiation displays at least six of the following reflections, quoted as degrees 2θ (±0.2 degrees) values 6.8, 7.0, 7.6, 8.3, 11.2, 11.3, 12.4, 12.8, 15.6, 16.5, 16.6, 17.4, 17.5, 18.5, 19.6, 20.1, 23.5, 24.2 and 26.7.

In another aspect the present disclosure provides a crystalline form of 4-amino-N-tert-butyl-4,5-dihydro-3-isopropyl-5-oxo-1,2,4-1H-triazole-1-carboxamide, characterized by an X-ray powder diffractogram using Cu-Kα radiation displays at least 3 of the following reflections, quoted as degrees 2θ (±0.2 degrees) values 6.8, 7.6, 8.3, 12.4, 12.8, 16.4, 16.5 and 17.5.

In another aspect the present disclosure provides a process for the production of a crystalline form C of 4-amino-N-tert-butyl-4,5-dihydro-3-isopropyl-5-oxo-1,2,4-1H-triazole-1-carboxamide, comprising:
  i) providing a solution of 4-amino-N-tert-butyl-4,5-dihydro-3-isopropyl-5-oxo-1,2,4-1H-triazole-1-carboxamide in an organic solvent;
  ii) effecting crystallisation by subjecting said solution to pre-determined crystallisation conditions thereby obtaining said crystalline form C.

In another aspect the present disclosure provides agrochemical composition comprising:
  i) a crystalline form C of 4-amino-N-tert-butyl-4,5-dihydro isopropyl-5-oxo-1,2,4-1H-triazole-1-carboxamide; and
  ii) at least one agrochemically acceptable carrier.

In another aspect the present disclosure provides a method for the control of undesired plant growth, comprising subjecting the plants or their locus to the action of a crystalline form C of 4-amino-N-tert-butyl-4,5-dihydro-3-isopropyl-5-oxo-1,2,4-1H-triazole-1-carboxamide.

DETAILED DESCRIPTION OF INVENTION

In any aspect or embodiment described hereinbelow, the phrase comprising may be replaced by the phrases "consisting of" or "consisting essentially of" or "consisting substantially of". As used herein in this context, the expression "substantially pure" will be understood to mean that the crystalline form contains less than 20% or less than 10% or less than 5% or less than 2% or less than 1% of any other form of the subject compound as measured, for example, by powder X-ray diffraction (PXRD). As used herein, the term "about" refers to a measurable value such as a parameter, an amount, a temporal duration, and the like and is meant to include variations of +/−15% or less, specifically variations of +/−10% or less, more specifically variations of +/−5% or less, even more specifically variations of +/−1% or less, and still more specifically variations of +1-0.1% or less of and from the particularly recited value, in so far as such variations are appropriate to perform in the disclosure described herein. Furthermore, it is also to be understood that the value to which the modifier "about" refers is itself specifically disclosed herein.

Inventors of the present disclosure provide a crystalline form of 4-amino-N-tert-butyl-4,5-dihydro-3-isopropyl-5-oxo-1,2,4-1H-triazole-1-carboxamide and process for preparing thereof.

The novel crystalline form of 4-amino-N-tert-butyl-4,5-dihydro-3-isopropyl-5-oxo-1,2,4-1H-triazole-1-carboxamide is hereafter referred as Form C. The terms, novel crystalline form of 4-amino-N-tert-butyl-4,5-dihydro-3-isopropyl-5-oxo-1,2,4-1H-triazole-1-carboxamide or 4-amino-N-tert-butyl-4,5-dihydro-3-isopropyl-5-oxo-1,2,4-1H-triazole-1-carboxamide Form C or crystalline Form C or Form C of Amicarbazone are used synonymously.

Figure 1:
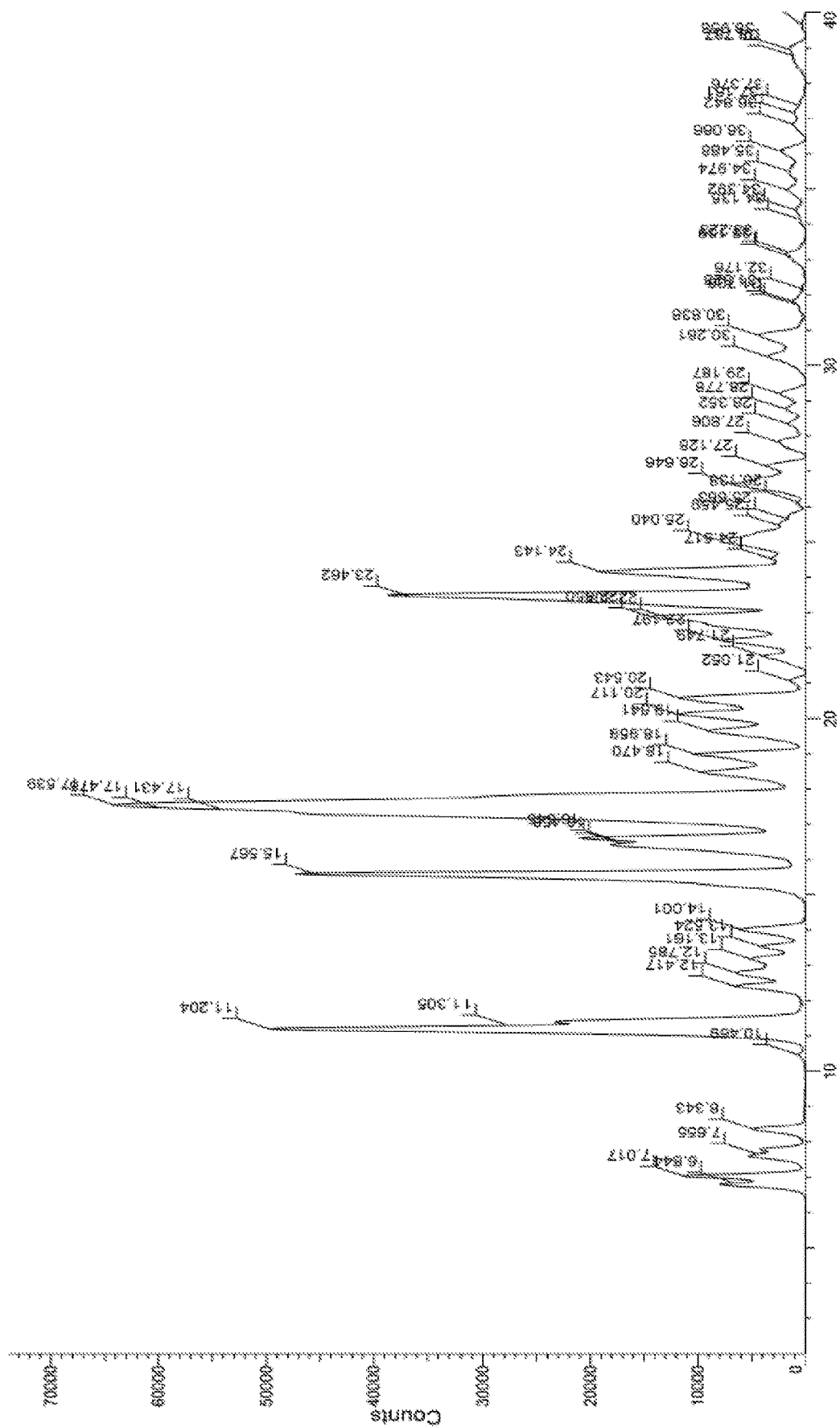
FIG. 1: X-ray powder diffractogram of form C of amicarbazone.
Figure 2:
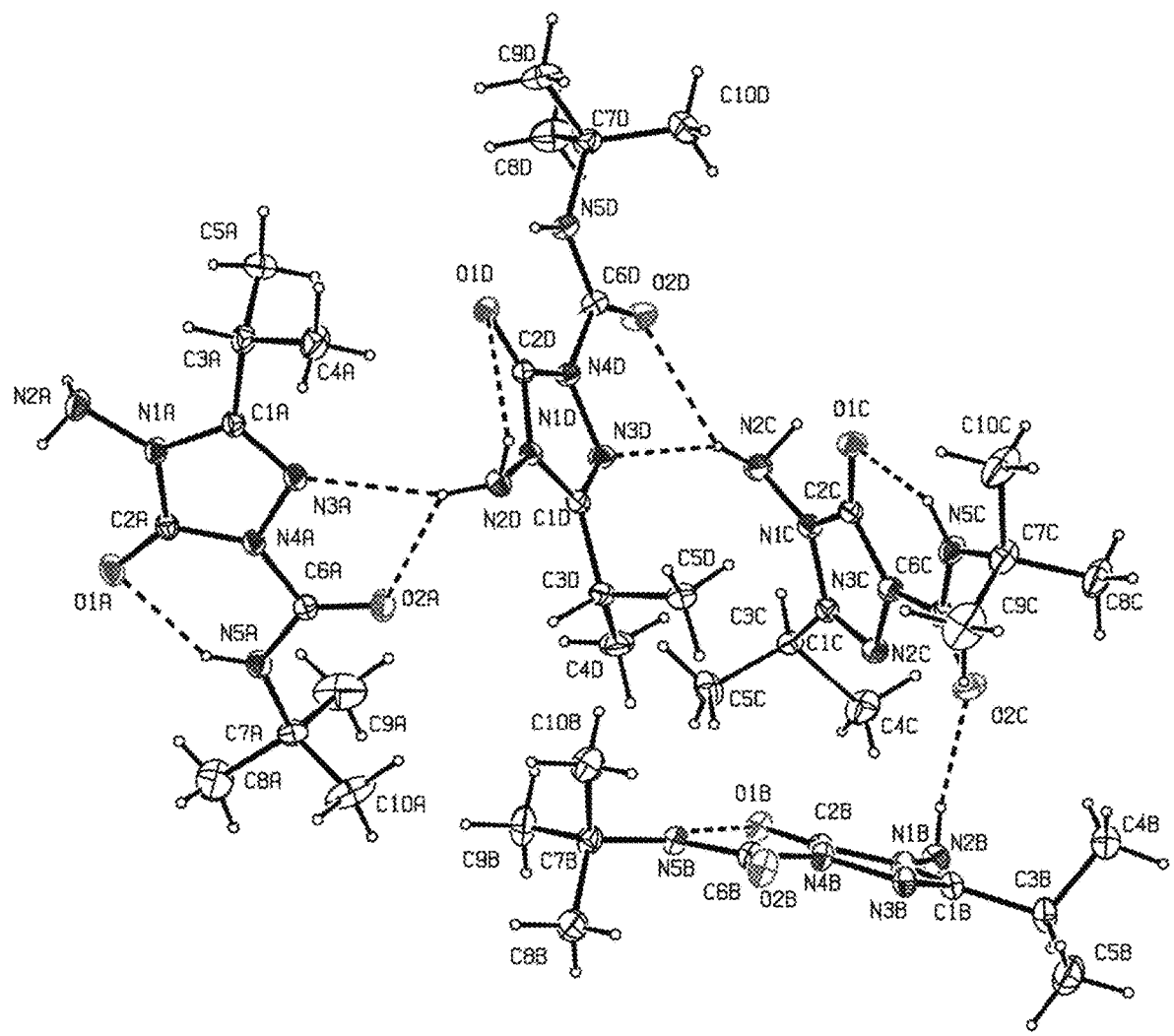
FIG. 2: Crystal structure of Form C of amicarbazone.

In one embodiment, the present disclosure provides a crystalline form of 4-amino-N-tert-butyl-4,5-dihydro-3-isopropyl-5-oxo-1,2,4-1H-triazole-1-carboxamide characterized by X-ray powder diffraction pattern which is substantially in accordance with FIG. 1.

Thus, in an embodiment there is provided a crystalline form C of 4-amino-N-tert-butyl-4,5-dihydro-3-isopropyl-5-oxo-1,2,4-1H-triazole-1-carboxamide, which in an X-ray powder diffractogram using Cu-Kα radiation displays at least three of the following reflections, quoted as degrees 2θ (±0.2 degrees) values 6.8, 7.0, 7.6, 8.3, 11.2, 11.3, 12.4, 12.8, 15.6, 16.5, 16.6, 17.4, 17.5, 18.5, 19.6, 20.1, 23.5, 24.2, and 26.7.

In an embodiment there is provided a crystalline form C of 4-amino-N-tert-butyl-4,5-dihydro-3-isopropyl-5-oxo-1,2,4-1H-triazole-1-carboxamide, which in an X-ray powder diffractogram using Cu-Kα radiation displays at least six of the following reflections, quoted as degrees 2θ (±0.2 degrees) values 6.8, 7.0, 7.6, 8.3, 11.2, 11.3, 12.4, 12.8, 15.6, 16.5, 16.6, 17.4, 17.5, 18.5, 19.6, 20.1, 23.5, 24.2 and 26.7.

In an embodiment there is provided a crystalline form C of 4-amino-N-tert-butyl-4,5-dihydro-3-isopropyl-5-oxo-1,2,4-1H-triazole-1-carboxamide, which in an X-ray powder diffractogram using Cu-Kα radiation displays all of the following reflections, quoted as degrees 2θ (±0.2 degrees) values 6.8, 7.0, 7.6, 8.3, 11.2, 11.3, 12.4, 12.8, 15.6, 16.5, 16.6, 17.4, 17.5, 18.5, 19.6, 20.1, 23.5, 24.2, and 26.7.

In another aspect the present disclosure provides a crystalline form of 4-amino-N-tert-butyl-4,5-dihydro-3-isopropyl-5-oxo-1,2,4-1H-triazole-1-carboxamide, characterized by an X-ray powder diffractogram using Cu-Kα radiation displays at least 3 of the following reflections, quoted as degrees 2θ (±0.2 degrees) values 6.8, 7.6, 8.3, 12.4, 12.8, 16.4, 16.5 and 17.5.

In another aspect the present disclosure provides a crystalline form of 4-amino-N-tert-butyl-4,5-dihydro-3-isopropyl-5-oxo-1,2,4-1H-triazole-1-carboxamide, characterized by an X-ray powder diffractogram using Cu-Kα radiation displays at least 5 of the following reflections, quoted as degrees 2θ (±0.2 degrees) values 6.8, 7.6, 8.3, 12.4, 12.8, 16.4, 16.5 and 17.5.

In another aspect the present disclosure provides a crystalline form of 4-amino-N-tert-butyl-4,5-dihydro-3-isopropyl-5-oxo-1,2,4-1H-triazole-1-carboxamide, characterized by an X-ray powder diffractogram using Cu-Kα radiation displays the following reflections, quoted as degrees 2θ (±0.2 degrees) values 6.8, 7.6, 8.3, 12.4, 12.8, 16.4, 16.5 and 17.5.

The characteristic unit cell parameters of the crystal structure of crystalline form C of 4-amino-N-tert-butyl-4,5-dihydro-3-isopropyl-5-oxo-1,2,4-1H-triazole-1-carboxamide is given in the below table (Table 1). The basic crystal structure is triclinic, and the unit cell has the space group P1. The asymmetric unit contains four crystallographically independent molecules (Z'=4).

TABLE 1

| | |
|---|---|
| Empirical formula | $C_{10}H_{19}N_5O_2$ |
| Formula weight | 241.30 |
| Temperature | 294(2) K |
| Wavelength | 0.71073 Å |
| Crystal system | Triclinic |
| Space group | P$\bar{1}$ |
| Unit cell dimensions | a = 15.4098(4) Å     α = 114.3935(8)°. |
| | b = 15.4932(4) Å     β = 94.5271 (8)°. |
| | c = 15.6125(4) Å     γ = 119.0913(8)°. |
| Volume | 2777.15(13) Å$^3$ |
| Z | 8 |
| Density (calculated) | 1.154 Mg/m$^3$ |
| Absorption coefficient | 0.083 mm$^{-1}$ |
| Final R indices [I > 2σ(I)] | R1 = 0.0619; wR2 = 0.1610 |
| R indices (all data) | R1 = 0.1001; wR2 = 0.1893 |

In an embodiment, the present crystalline form C has the following lattice parameters: a=15.4098(4), b=15.4932(4), c=15.6125(4), α=114.3935(8°), β=94.5271 (8°), γ=119.0913(8°) and volume=2777.15(13) Å$^3$.

Figure 3:
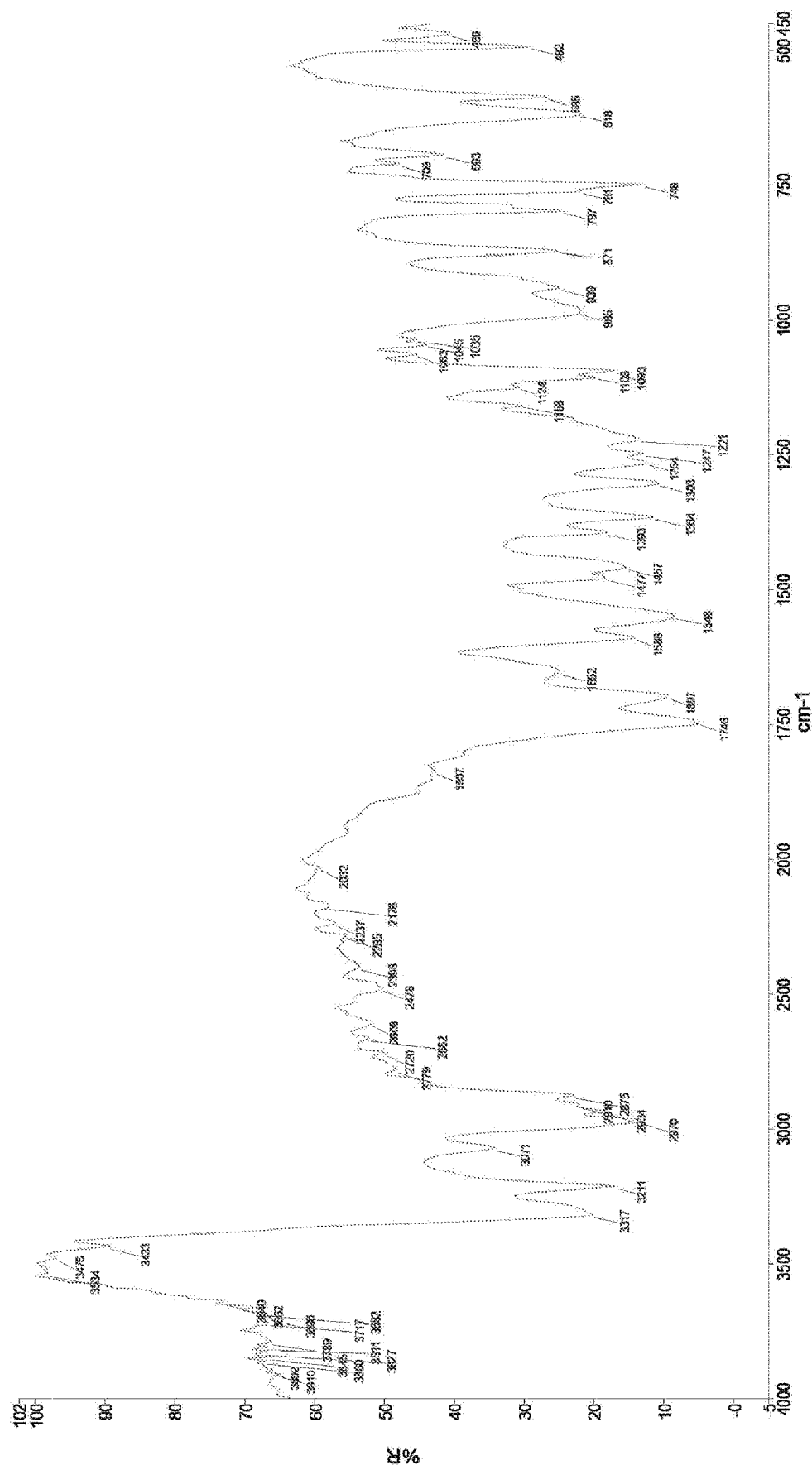
FIG. 3: Fourier-Transform Infra-Red (FTIR) spectrum of amicarbazone.

In one embodiment, the present disclosure provides a crystalline form of 4-amino-N-tert-butyl-4,5-dihydro-3-isopropyl-5-oxo-1,2,4-1H-triazole-1-carboxamide characterized by a Fourier-Transform Infra-Red (FTIR) spectrum which is substantially in accordance with FIG. 3.

In an embodiment, crystalline form C of 4-amino-N-tert-butyl-4,5-dihydro-3-isopropyl-5-oxo-1,2,4-1H-triazole-1-carboxamide exhibits a Fourier-Transform Infra-Red (FTIR) spectrum with characteristic peaks at wavenumbers (cm$^{-1}$±0.2%) of 3317, 3211, 3071, 2934, 2477, 1648, 1393, 1106, 986, 939 and 617.

In an embodiment, crystalline form C of 4-amino-N-tert-butyl-4,5-dihydro-3-isopropyl-5-oxo-1,2,4-1H-triazole-1-carboxamide exhibits an Infra-Red(IR) spectrum with characteristic peaks at wavenumbers (cm$^{-1}$±0.2%) of 3648, 3477, 3433, 3317, 3211, 3071, 2934, 2910, 2779, 2662, 2477, 2285, 2237, 2032, 1648, 1393, 1158, 1106, 986, 939, 709, 617 and 470.

Figure 4:
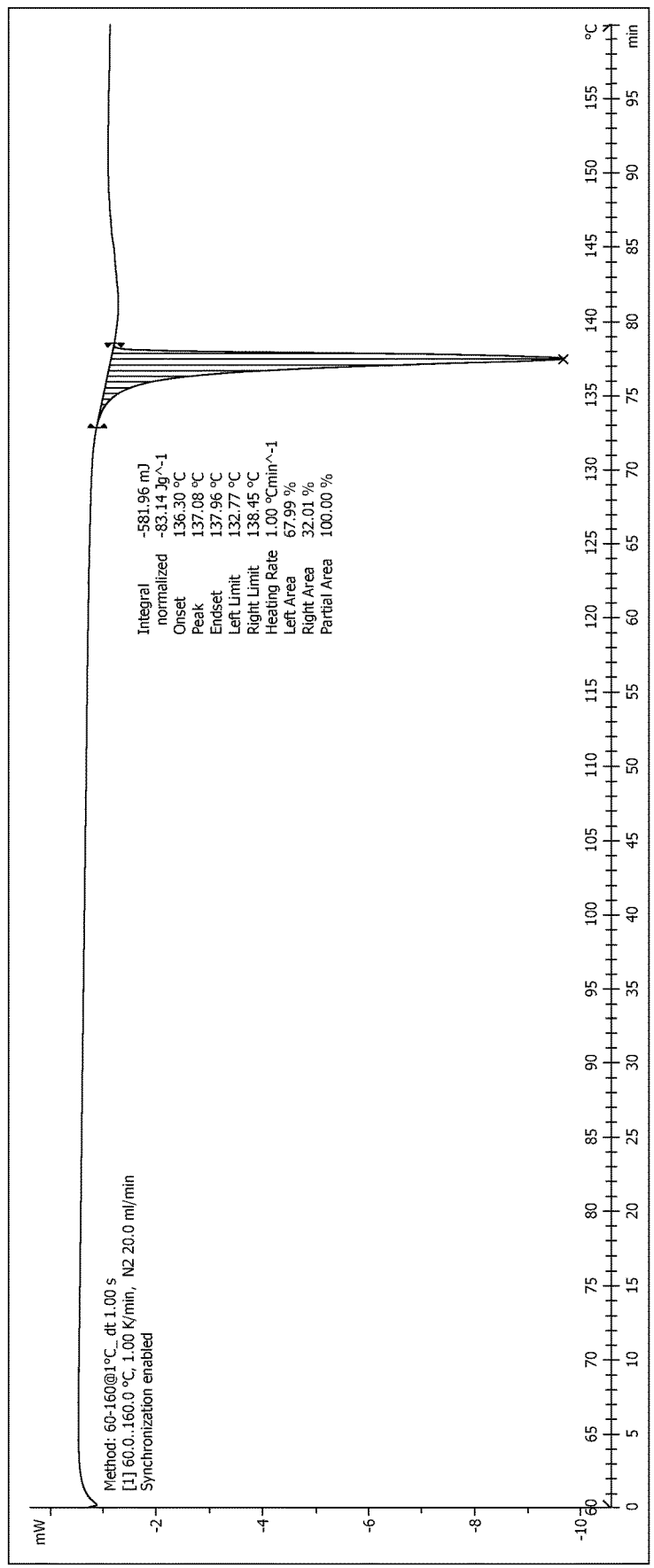
FIG. 4: Differential scanning calorimetry (DSC) thermogram of form C of amicarbazone.

In one embodiment, the present disclosure provides a crystalline form of 4-amino-N-tert-butyl-4,5-dihydro-3-isopropyl-5-oxo-1,2,4-1H-triazole carboxamide characterized by differential scanning calorimetry endotherm curve, which is substantially in accordance with FIG. 4.

In one embodiment, the present disclosure provides a crystalline form of 4-amino-N-tert-butyl-4,5-dihydro-3-isopropyl-5-oxo-1,2,4-1H-triazole-1-carboxamide characterized by differential scanning calorimetry endotherm curve having an endothermic peak at about 133° about 138° C.

In an embodiment there is provided a crystalline form C of 4-amino-N-tert-butyl-4,5-dihydro-3-isopropyl-5-oxo-1,2,4-1H-triazole-1-carboxamide which displays a DSC thermogram with a characteristic melting endothermic peak at about 137° C., specifically 137.08° C.

In an embodiment, said crystalline form C is characterized by a powder X-ray diffraction pattern substantially in accordance with FIG. 1. Further said crystalline form is characterized by Fourier-Transform Infra-Red (FTIR) spectrum substantially in accordance with FIG. 3. Further said crystalline form is characterized by DSC thermogram substantially in accordance with FIG. 4.

In another aspect the present disclosure provides substantially pure form C of 4-amino-N-tert-butyl-4,5-dihydro-3-isopropyl-5-oxo-1,2,4-1H-triazole-1-carboxamide.

In an embodiment, a crystalline form of 4-amino-N-tert-butyl-4,5-dihydro-3-isopropyl-5-oxo-1,2,4-1H-triazole-1-carboxamide characterized by one or more data selected from
- an X-ray powder diffractogram having at least three of the following reflections values 6.8, 7.0, 7.6, 8.3, 11.2, 11.3, 12.4, 12.8, 15.6, 16.5, 16.6, 17.4, 17.5, 18.5, 19.6, 20.1, 23.5, 24.2 and 26.7 degrees 2θ (±0.2 degrees);
- an X-ray powder diffractogram pattern substantially as depicted in FIG. 1;
- a Fourier-Transform Infra-Red spectrum with characteristic peaks at wavenumbers (cm$^{-1}$±0.2%) of 3317, 3211, 3071, 2934, 2477, 1648, 1393, 1106, 986, 939 and 617;
- a differential scanning calorimetry endotherm curve having an endothermic peak at about 133° to about 138° C.;
- a differential Scanning calorimetry thermogram substantially as depicted in FIG. 4 and combinations thereof.

In another aspect the present disclosure provides a process for preparing form C of amicarbazone.

In an embodiment the process for production of a crystalline form C of 4-amino-N-tert-butyl-4,5-dihydro-3-isopropyl-5-oxo-1,2,4-1H-triazole-1-carboxamide, comprising:
i) providing a solution of 4-amino-N-tert-butyl-4,5-dihydro-3-isopropyl-5-oxo-1,2,4-1H-triazole-1-carboxamide in an organic solvent; and
ii) effecting crystallisation by subjecting said solution to pre-determined crystallisation conditions to obtain crystalline form C.

In an embodiment, solvent suitable for preparing the solution is selected from hydrocarbon solvents, halogenated hydrocarbons, alcohols, ketones, ester solvent or mixtures thereof.

In a specific embodiment, solvent suitable for preparing the solution is selected from toluene, dichloromethane, dichloroethane, methanol, ethanol, isopropanol, acetone, ethyl acetate or mixtures thereof.

In an embodiment the concentration of 4-amino-N-tert-butyl-4,5-dihydro isopropyl-5-oxo-1,2,4-1H-triazole-1-carboxamide solution depends upon the nature of the solvent.

In an embodiment a saturated solution is used.

In an embodiment the solution is prepared by mixing 4-amino-N-tert-butyl-4,5-dihydro-3-isopropyl-5-oxo-1,2,4-1H-triazole-1-carboxamide in a suitable solvent at a temperature in the range from about 25° C. to about 100° C.

In a specific embodiment the solution is prepared at a temperature in the range from about 30° C. to about 80° C.

In another embodiment the solution is prepared using any known form of 4-amino-N-tert-butyl-4,5-dihydro-3-isopropyl-5-oxo-1,2,4-1H-triazole-1-carboxamide, e.g. crystalline form A.

In another embodiment the solution is prepared using 4-amino-N-tert-butyl-4,5-dihydro-3-isopropyl-5-oxo-1,2,4-1H-triazole-1-carboxamide prepared by methods known to a skilled person.

In an embodiment the crystallisation is performed by subjecting the solution to cooling at pre-determined rates.

In an embodiment the crystallisation is performed by preparing a solution at a first temperature followed by subjecting the solution to a second temperature at a pre-determined rate.

Thus, in an embodiment there is provided a process for the production of a crystalline form C of 4-amino-N-tert-butyl-4,5-dihydro-3-isopropyl-5-oxo-1,2,4-1H-triazole-1-carboxamide, said process comprising:
i) providing a solution of 4-amino-N-tert-butyl-4,5-dihydro isopropyl-5-oxo-1,2,4-1H-triazole-1-carboxamide in an organic solvent at a first temperature;
ii) effecting crystallisation by subjecting the said solution to a second temperature at a pre-determined rate thereby obtaining said crystalline form C.

In an embodiment, solvent suitable is selected from hydrocarbon solvents, halogenated hydrocarbons, alcohols, ketones, ester solvents or mixtures thereof.

In a specific embodiment, the solvent is selected from toluene, dichloromethane, dichloroethane, methanol, ethanol, isopropanol, acetone, ethyl acetate or mixtures thereof.

In an embodiment the crystallisation is performed by preparing a solution of 4-amino-N-tert-butyl-4,5-dihydro-3-isopropyl-5-oxo-1,2,4-1H-triazole-1-carboxamide in an organic solvent at a first temperature in the range from about 30° C. to about 100° C.

In an embodiment the crystallisation is performed by subjecting the solution of 4-amino-N-tert-butyl-4,5-dihydro-3-isopropyl-5-oxo-1,2,4-1H-triazole-1-carboxamide in an organic solvent to a second temperature in the range from about −20° C. to about 30° C.

In an embodiment the crystallisation is performed by subjecting the solution to low temperature, specifically at least 10° C. lower than the first temperature at which the solution is prepared.

In an embodiment the second temperature is in the range of about −20° to about 30° C.

In an embodiment the second temperature is in the range of about 0° C. to about 30° C.

In an embodiment crystallisation initiation occurs at the second temperature.

In an embodiment the solution is subjected to the second temperature at a pre-determined rate in the range of about 1° C. to about 5° C. per minute of change from the first temperature.

In an embodiment the solution is subjected to a temperature in the range of about 0° to about 30° C. at a pre-determined rate in the range of about 2° C. to about 5° C. per minute of cooling from the first temperature.

In an embodiment the solution is subjected to sub-zero temperature for completing crystallisation, for example at a sub-zero temperature of below 0° C. to about −20° C.

In an embodiment the crystallised form C of amicarbazone is isolated by separation of form C of amicarbazone from the mother liquor by normal techniques for the separation of solid components from liquids, by filtration, centrifugation or by decantation.

In an embodiment the crystallisation is performed by subjecting the solution to evaporation at a pre-determined rate.

Thus, in an embodiment there is provided a process for the production of a crystalline form C of 4-amino-N-tert-butyl-4,5-dihydro-3-isopropyl-5-oxo-1,2,4-1H-triazole-1-carboxamide, comprising:
  i) providing a solution of 4-amino-N-tert-butyl-4,5-dihydro-3-isopropyl-5-oxo-1,2,4-1H-triazole-1-carboxamide in an organic solvent;
  ii) effecting crystallisation by subjecting said solution to evaporation thereby obtaining said crystalline form C.

In an embodiment, solvent suitable is selected from hydrocarbon solvents, halogenated hydrocarbons, alcohols, ketones, ester solvents or mixtures thereof.

In a specific embodiment, the solvent is selected from the group comprising toluene, dichloromethane, dichloroethane, methanol, ethanol, isopropanol, acetone, ethyl acetate or mixtures thereof.

In an embodiment the solution is subjected to evaporation at ambient temperature and pressure conditions.

In another embodiment the evaporation is carried out over a prolonged period.

In another embodiment the evaporation is carried out over a time period of about 2 hours to about 72 hours.

In another embodiment the evaporation is carried out over a time period of about 4 hours to about 48 hours.

In an embodiment the crystallized form C of amicarbazone is obtained by evaporation of the solution to dryness.

In an embodiment the crystalline form C produced according to the present disclosure is having purity more than 98% specifically more than 99%, e.g. as measured by HPLC.

The present disclosure further provides an agrochemical composition comprising
  i) a crystalline form C of 4-amino-N-tert-butyl-4,5-dihydro isopropyl-5-oxo-1,2,4-1H-triazole-1-carboxamide; and
  ii) at least one agrochemically acceptable carrier.

In an embodiment the compositions according to the present disclosure comprises form C of amicarbazone in an amount from about 5% to about 99% by weight of the composition.

In an embodiment the agrochemically acceptable carrier/additives are selected from adjuvants or surfactants including but not limited to wetting agents, emulsifiers, dispersants, viscosity-modifying agents, antifoaming agents, antifreeze agents, pH adjusting agents, stabilizers, anticaking agents, biocides and the like.

In an embodiment the compositions according to the present disclosure can be in the form of aqueous suspension concentrates, oil dispersions or oil-based suspensions, water-dispersible powders or granules.

In an embodiment the compositions according to the present disclosure can be in the solid form of water-dispersible powders and granules, e.g. coated, impregnated and homogeneous granules.

In an embodiment such solid compositions can comprise a crystalline form C of amicarbazone and solid carriers.

In an embodiment the solid composition can be produced by spray-drying, extrusion processes, fluidized bed granulation, spray granulation and other such comparable technologies.

In an embodiment the compositions according to the present disclosure further comprises one or more other active ingredients.

In an embodiment the active ingredients that can be present in the compositions according to the present disclosure is selected from but not limited to herbicides, fungicides, insecticides and plant growth regulators.

In an embodiment the herbicide that can be present in the compositions according to the present disclosure can be selected from: diphenyl ether herbicides such as oxyfluorfen, acifluorfen and its salts, lactofen and its salts, fomesafen and its salts; Pyrimidinyloxybenzoic analogue herbicides such as pyrithiobac sodium, bispyribac sodium; Organophosphrous based herbicides such as glyphosate and its salts, bilanafos and its salts, bialaphos and its salts; Bipyridinium herbicides such as paraquat and diquat and salts thereof; aryloxyalkanoic acid herbicides such as 2, 4-D and its salts and esters, MCPA, MCPB and their salts; aryloxyphenoxypropionic herbicides such as haloxyfop, isomers and esters, clodinafop and its esters; Pyridine herbicides such as triclopyr, picloram, aminopyralid and salts thereof; Aromatic herbicides such as dicamba, 2,3,6-TBA, tricamba and their salts; Pyridinecarboxylic acid herbicides such as clopyralid; Imidazolinones selected from imazameth, imazamethabenz, imazamox, imazapic, imazapyr, imazaquin, imazethapyr; herbicides such as sulfonyl urea herbicides such as flazasulfuron, rimsulfuron, bensulfuron, ethoxysulfuron, mesosulfuron, oxasulfuron, pyrazosurfuron-ethyl and their salts; cyclohexanedione oxime herbicides such as clethodim and its salts, chloroacetamide herbicide such as metolachlor and its salts and isomers, phenyl phthalimide herbicides such as flumioxazin and its salts, mesotrione, dinitroaniline herbicides such as oryzalin, pendimethalin, profluralin, trifluralin and its salts, bicyclic dicarboxylic acid herbicides such as endothal and its salts or mixtures of such herbicides.

In an embodiment suitable herbicides may be selected from acetochlor, acifluorfen, aclonifen, alachlor, ametryn, amidosulfuron, aminopyralid, amitrole, anilofos, asulam, atrazine, azafenidin, azimsulfuron, benazolin, benfluralin, bensulfuron-methyl, bentazone, bifenox, binalafos, bispyribac-sodium, bromacil, bromoxynil, butachlor, butroxidim, cafenstrole, carbetamide, carfentrazone-ethyl, chloridazon, Chlorimuron-ethyl, chlorobromuron, chlorotoluron, chlorsulfuron, cinidon-ethyl, cinosulfuron, clethodim, Clomazone, Clopyralid, Cloransulam-methyl, Clorsulfuron, Cyanazine, Cycloate, Cyclosulfamuron, Cycloxydim, Dalapon, Desmedipham, Dicamba, Dichlobenil, Dichlormid, Diclosulam, Diflufenican, Dimefuron, Dimepipeate, Dimethachlor, Dimethenamid, Diquat, Diuron, Esprocarb, Ethalfluralin, Ethametsulfuron-methyl, Ethofumesate, Ethoxysulfuron, Fentrazamide, Flazasulfuron, Florasulam, Fluchloralin, Flufenacet, Flumetsulam, Flumioxazin, Fluometuron, Flupyrsulfuron-methyl, Fluorochloridone, Fluoroxypyr, Flurtamone, Fomesafen, Foramsulfuron, Hexazinone, Imazamethabenz-m, Imazamox, mazapic, Imazapyr, Imazaquin, Imazethapyr, Imazosulfuron, lodosulfuron, loxynil, Isoproturon, Isoxaben, Isoxaflutole, Lactofen, Lenacil, Linuron, Mefenacet, Mesosulfuron-Methyl, Mesotrione, tembotrione, topramezone, Metamitron, Metazachlor, Methabenzthiazuron, Metobromuron, Metolachlor, S-metolachlor Metosulam, Metoxuron, Metribuzin, Metsulfuron-methyl, Molinate, MSMA, Napropamide, Nicosulfuron, Norflurazon, Oryzalin, Oxadiargyl, Oxadiazon, Oxasulfuron, Oxyfluorfen, Paraquat, Pendimethalin, Phenmedipham, Picloram, Pretilachlor, Profoxydim, Prometryn, Propanil, Propisochlor, Propoxycarbazone, Propyzamide, Prosulfocarb, Prosulfuron, Pyraflufen-ethyl, Pyrazosulfuron, Pyroxasulfone, Pyridate, Pyrithiobac, Quinclorac, Quinmerac, Quinotrione, Rimsulfuron, Sethoxydim, Simazine, Sulcotrione, Sulfentrazone, Sulfosulfuron, Tebuthiuron, Tepraloxydim, Terbuthylazine, Terbutryn, Thifensulfuron-methyl, Thiobencarb, Tralkoxydim, Triallate, Triasulfuron, Tribenuron-methyl, Triclopyr, Trifloxysulfuron, Trifluralin and mixtures and combinations thereof.

In an embodiment suitable herbicides may be selected from the group comprising topramezone, orthosulfamuron, pinoxaden, metamifop, pyrimisulfan, tembotrione, thiencarbazone methyl, flucetosulfuron, aminopyralid, pyrasulfotole, saflufenacil, pyroxsulam, pyroxasulfone, pyraclonil, indaziflam, fenquinotrione, florpyrauxifen-benzyl, tiafenacil, cinmethylin, lancotrione-sodium, bixlozone, trifludimoxazin, cyclopyrimorate, methiozolin, am inocyclopyrachlor, metazosulfuron, ipfencarbazone, fenoxasulfone, bicyclopyrone, triafamone, halauxifen methyl, tolpyralate or combinations thereof.

In an embodiment the present disclosure provides a process for preparing an agrochemical composition comprising
i) a crystalline form C of 4-amino-N-tert-butyl-4,5-dihydro-3-isopropyl-5-oxo-1,2,4-1H-triazole-1-carboxamide; and
ii) one or more additives conventional for the formulation of plant protection agents;
wherein said process comprising admixing a crystalline form C of 4-amino-N-tert-butyl-4,5-dihydro-3-isopropyl-5-oxo-1,2,4-1H-triazole-1-carboxamide with one more said additives and formulating into suitable form.

The present disclosure further provides a method for the control of undesired plant growth, comprising subjecting the plants or their locus to the action of a crystalline form C of 4-amino-N-tert-butyl-4,5-dihydro-3-isopropyl-5-oxo-1,2,4-1H-triazole-1-carboxamide.

In an embodiment, there is provided a method for the control of undesired plant growth, comprising subjecting the plants or their locus to the action of a composition comprising:
i) a crystalline form C of 4-amino-N-tert-butyl-4,5-dihydro-3-isopropyl-5-oxo-1,2,4-1H-triazole-1-carboxamide; and
ii) one or more additives conventional for the formulation of plant protection agents.

Analytical Methods
Instrumental Details of Single Crystal XRD:
X-ray data for Amicarbazone form C was collected at room temperature on a Bruker D8 QUEST instrument with an IµS Mo microsource (λ=0.7107 Å) and a PHOTON-100 detector.

Instrumental Details of FTIR:
PerkinElmer make Spectrum Two™ FTIR instrument has been used in DRS mode.

Instrumental Details for X-Ray Powder Diffractogram:
X-ray powder diffractogram of amicarbazone form C was recorded using Cu-Kα radiation. X-ray powder diffraction method (PXRD) pattern was carried out on:
Instrument: Bruker make 2nd generation D2 Phaser Powder X-Ray diffractometer;
Operated at: 30.0 kV, 10 mA;
Radiation: Cu Kα;
Mode: Reflection
Wavelength: 1.54060° A,
Scan Range: 2-40 2θ,
Step size: 0.02°

Instrumental Details for DSC:
Instrument: Differential Scanning calorimeter Mettler Toledo DSC-3
Heating rate: 1° C./min
Temperature range: 60° C. to 160° C., under $N_2$ flow of 20 ml/min The instant invention is more specifically explained by below examples. However, it should be understood that the scope of the present invention is not limited by the examples in any manner. It will be appreciated by any person skilled in this art that the present invention includes aforesaid examples and further can be modified and altered within the technical scope of the present invention.

Examples

Preparation of Crystalline Form of Amicarbazone

Example 1

Preparation of a crystalline form C of 4-amino-N-tert-butyl-4,5-dihydro isopropyl-5-oxo-1,2,4-1H-triazole-1-carboxamide (amicarbazone)

Figure 5:
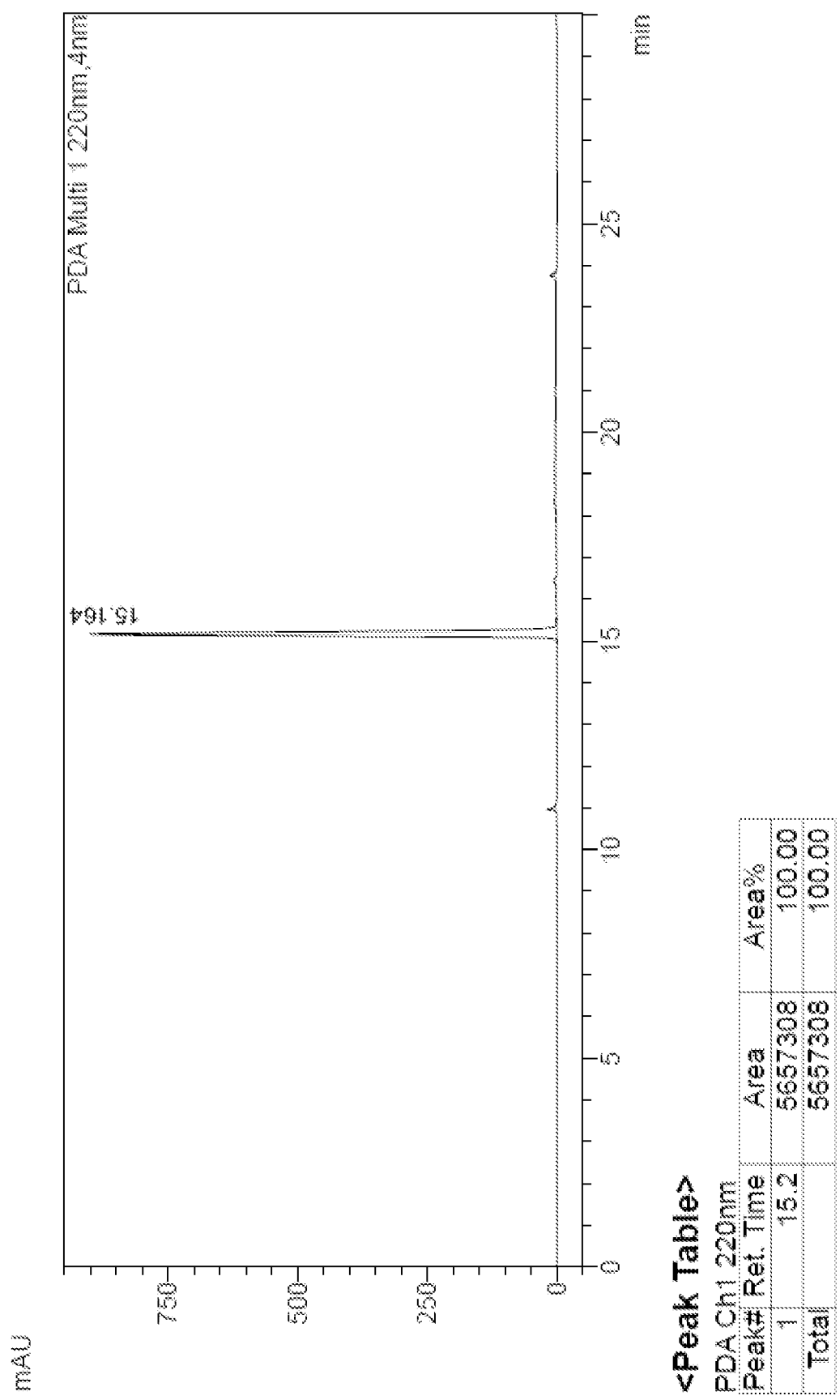
FIG. 5: High performance liquid chromatography) HPLC) of form C of amicarbazone.

2 g of amicarbazone (prepared according to U.S. Pat. No. 5,194,085) was dissolved in 20 ml of toluene at 40° C. The solution was stirred at 40° C. for 1 hour and filtered. The filtrate was brought to 25-30° C. and checked for crystallisation initiation. The resulting slurry was then stirred at 0-10° C. for 30 minutes. The precipitated solid was filtered out and dried at 50° C. to get 1.42 g of crystalline form of 4-amino-N-tert-butyl-4,5-dihydro-3-isopropyl-5-oxo-1,2,4-1H-triazole-1-carboxamide. Purity: 100% by HPLC (FIG. 5).

Example 2

2 g of amicarbazone (prepared according to U.S. Pat. No. 5,708,184) was dissolved in 10 ml of methylene dichloride at 40° C. The solution was stirred at 40° C. for 1 hour and filtered. The filtrate was brought to 25-30° C. at a rate of 2° C./min to initiate crystallisation. The resulting slurry was then stirred at 0-10° C. for 30 min. The precipitated solid was filtered out and dried at 50° C. to get 0.78 g of crystalline form C of 4-amino-N-tert-butyl-4,5-dihydro-3-isopropyl-5-oxo-1,2,4-1H-triazole-1-carboxamide.

Example 3

1 g of amicarbazone (prepared according to U.S. Pat. No. 5,194,085) was dissolved in 15 mL of methylene dichloride at 35° C. on a hotplate. The solution was filtered and left overnight for evaporation of the solvent in a 25 mL beaker. Crystals appeared were collected to get 0.8 g of crystalline form C of 4-amino-N-tert-butyl-4,5-dihydro-3-isopropyl-5-oxo-1,2,4-1H-triazole-1-carboxamide.

Example 4

25 mg of amicarbazone (prepared according to U.S. Pat. No. 5,708,184) was dissolved in 1 mL of ethyl acetate at 35° C. on a hotplate. The solution was filtered and left overnight for evaporation of the solvent in a 5 mL beaker. Crystals appeared were collected to get crystalline form C of 4-amino-N-tert-butyl-4,5-dihydro-3-isopropyl-5-oxo-1,2,4-1H-triazole-1-carboxamide.

Compositions:

Example 5: Composition comprising crystalline form C of 4-amino-N-tert-butyl-4,5-dihydro-3-isopropyl-5-oxo-1,2,4-1H-triazole-1-carboxamide

| Sr. No. | Ingredient | Quantity |
|---|---|---|
| 1 | Crystalline form C of amicarbazone | 143.80 |
| 2 | Citric acid | 1 |
| 3 | Silicon dioxide | 4 |
| 6 | Morwet 400 | 40 |
| 7 | Ammonium sulphate | 11.20 |

Process of Preparation of the Composition:

Required quantity of crystalline form C of amicarbazone, Citric acid, Silicon dioxide, Morwet 400 and ammonium sulphate were mixed and ground in air jet mill. Water was added in an amount sufficient to make dough and subjected to granulation in a granulator. The granules were dried using a fluidized bed dryer.

Example 6: Composition Comprising Crystalline Form C of 4 Amicarbazone

| Sr. No. | Ingredient | Quantity |
|---|---|---|
| 1 | Crystalline form C of amicarbazone | 70.5 |
| 2 | Citric acid | 0.5 |
| 3 | Precipitated silica | 2.0 |
| 4 | PVP K 30 | 2.0 |
| 5 | Sodium lauryl sulfate | 8.0 |
| 6 | Morwet 400 | 10 |
| 7 | Ammonium sulphate | 7.0 |
| | Total | 100 |

The composition was prepared by following the process of example 5.

Example 7: Composition of Amicarbazone Prepared According to U.S. Pat. No. 5,708,184

| Sr. No. | Ingredient | Quantity |
|---|---|---|
| 1 | Amicarbazone form A | 71.0 |
| 2 | Citric acid | 0.5 |
| 3 | Precipitated silica | 2.0 |
| 4 | PVP K 30 | 2.0 |
| 5 | Sodium lauryl sulfate | 8.0 |
| 6 | Morwet 400 | 10 |
| 7 | Ammonium sulphate | 6.5 |
| | Total | 100 |

Amicarbazone Form A preparation: Amicarbazone was prepared according to U.S. Pat. No. 5,708,184. The resulting compound was recrystallized from methyl t-butyl ether to get amicarbazone Form A.

The composition was prepared by following the process of example 5.

Example 8

Field Trial Data:

I] Field trials were carried out using water dispersible granular formulation comprising form C of 4-amino-N-tert-butyl-4,5-dihydro-3-isopropyl-5-oxo-1,2,4-1H-triazole-1-carboxamide prepared according to the present disclosure as the broad spectrum herbicide. The compositions were dispersed with water and optionally with other tank mix auxiliaries and applied at a water application rate of 500 liters per hectare (l/ha) to crop and non-crop land containing many broad leave weeds, grasses and sedges.

Inventors carried out field trials using samples prepared according to Example 6 (Sample 1) and compared it with a sample prepared according to Example 7 (Sample 2). The results are summarised below:

| Crop: | Sugarcane |
|---|---|
| Target weeds: | *Ipomea hederacea*, *Setaria* sp, *Wild okra*, *Euphorbia geniculata* |
| Water Volume: | 500 L/ha |
| Nozzle: | Flat Fan Nozzle |

TABLE 2

% weed control after 5 days after application

| Sample | *Ipomea hederacea* | *Setaria* sp | *Wild okra* |
|---|---|---|---|
| | % Weed control Dose: 1000 g/ha | | |
| Sample 1 | 7.5 | 5.0 | 9.0 |
| Sample 2 | 8.0 | 4.5 | 9.0 |
| | Dose: 1500 g/ha | | |
| Sample 1 | 8 | 5.0 | — |
| Sample 2 | 8.5 | 5.5 | — |

TABLE 3

% weed control after 12 days after application

| Sample | *Ipomea Hederacea* | *Setaria* sp | *Wild okra* |
|---|---|---|---|
| | % Weed control Dose: 1000 g/ha | | |
| Sample 1 | 8.0 | 4.0 | 9.0 |
| Sample 2 | 8.5 | 5.0 | 9.0 |
| | Dose: 1500 g/ha | | |
| Sample 1 | 8.5 | 5.0 | — |
| Sample 2 | 9.0 | 6.0 | — |

It has been evident from the above table the composition according to the present disclosure exhibited acceptable weed control against various persistent weeds. It has been further noted that performance of the composition comprising Form C is equally effective in controlling the weeds compared to known form A of amicarbazone. However, it was noted that the formulation prepared using known form A of amicarbazone induces phytotoxicity to the crops. To further understand the effect of crystalline form C of amicarbazone in crops a field test has been conducted and the observation is discussed as follows:

II] Phytotoxicity effect crystalline form C of 4-amino-N-tert-butyl-4,5-dihydro-3-isopropyl-5-oxo-1,2,4-1H-triazole-1-carboxamide on crop Inventors carried out field testing in tomato plants using samples prepared according to Example 6 (Sample 1) and compared it with a sample prepared according to Example 7 (Sample 2). It has been observed that the composition comprising crystalline Form C is inducing less phytotoxic effect on tomato plants. The result is summarized below.

TABLE 4

| % Phytotoxicity on tomato plant | | |
| --- | --- | --- |
| Sample No | Dose g/ha | % crop injury (5DAA) |
| Sample 1 | 1500 | 20 |
| Sample 2 | 1500 | 35 |

Thus, it has been established that crystalline form of 4-amino-N-tert-butyl-4,5-dihydro-3-isopropyl-5-oxo-1,2,4-1H-triazole-1-carboxamide is highly efficacious for controlling weeds as well in imparting safety to the crops.

We claim:

1. A crystalline form C of 4-amino-N-tert-butyl-4,5-dihydro-3-isopropyl-5-oxo-1,2,4-1H-triazole-1-carboxamide characterized by an X-ray powder diffractogram comprising at least three reflections values selected from the group consisting of 6.8, 7.0, 7.6, 8.3, 11.2, 11.3, 12.4, 12.8, 15.6, 16.5, 16.6, 17.4, 17.5, 18.5, 19.6, 20.1, 23.5, 24.2 and 26.7 degrees 2θ (±0.2 degrees); and a Fourier-Transform Infra-Red spectrum comprising characteristic peaks at wavenumbers ($cm^{-1}$±0.2%) of 3317, 3211, 3071, 2934, 2477, 1648, 1393, 1106, 986, 939 and 617.

2. The crystalline form C of 4-amino-N-tert-butyl-4,5-dihydro-3-isopropyl-5-oxo-1,2,4-1H-triazole-1-carboxamide according to claim 1, wherein the crystalline form is characterized by an X-ray powder diffractogram pattern comprising at least six of reflections values selected from the group consisting of 6.8, 7.0, 7.6, 8.3, 11.2, 11.3, 12.4, 12.8, 15.6, 16.5, 16.6, 17.4, 17.5, 18.5, 19.6, 20.1, 23.5, 24.2 and 26.7 degrees 2θ (±0.2 degrees).

3. A process for the production of the crystalline form C of 4-amino-N-tert-butyl-4,5-dihydro-3-isopropyl-5-oxo-1,2, 4-1H-triazole-1-carboxamide according to claim 1, the process comprising:

i) providing a solution of 4-amino-N-tert-butyl-4,5-dihydro-3-isopropyl-5-oxo-1,2,4-1H-triazole-1-carboxamide in an organic solvent at a first temperature;

ii) effecting crystallisation by subjecting said solution to a second temperature at a pre-determined rate, the predetermined rate ranging from 1° C. to 5° C. per minute of cooling from the first temperature thereby obtaining said crystalline form C.

4. The process according to claim 3, wherein said first temperature is in a range from 30° C. to 100° C.

5. The process according to claim 3, wherein said second temperature is in a range from 20° C. to 30° C.

6. The process according to claim 3, wherein said organic solvent is selected from the group consisting of hydrocarbon solvents, halogenated hydrocarbons, alcohols, ketones, ester solvent, and a mixture thereof.

7. An agrochemical composition comprising:

i) the crystalline form C of 4-amino-N-tert-butyl-4,5-dihydro-3-isopropyl-5-oxo-1,2,4-H-triazole-1-carboxamide according to claim 1; and ii) at least one agrochemically acceptable carrier.

8. The agrochemical composition according to claim 7 wherein said composition comprises the crystalline form C of 4-amino-N-tert-butyl-4,5-dihydro-3-isopropyl-5-oxo-1,2, 4-1H-triazole-1-carboxamide in an amount ranging from 1% to 99% by weight of the composition.

9. The agrochemical composition according to claim 7, wherein said composition is a solid formulation.

10. A method for controlling undesired plant growth comprising applying to the plant or its locus a crystalline form C of 4-amino-N-tert-butyl-4,5-dihydro-3-isopropyl-5-oxo-1,2,4-1H-triazole-1-carboxamide according to claim 1.

11. The method according to claim 10, wherein said method comprises applying to the plant or its locus an agrochemical composition comprising:

i) the crystalline form of 4-amino-N-tert-butyl-4,5-dihydro-3-isopropyl-5-oxo-1,2,4-1H-triazole-1-carboxamide; and ii) at least one agrochemically acceptable carrier.

12. The crystalline form C of 4-amino-N-tert-butyl-4,5-dihydro-3-isopropyl-5-oxo-1,2,4-1H-triazole-1-carboxamide according to claim 1, wherein the crystalline form is further characterized by a differential scanning calorimetry endotherm curve comprising an endothermic peak at 133° C. to 138° C.

* * * * *